(12) United States Patent
Prakash et al.

(10) Patent No.: US 11,033,006 B2
(45) Date of Patent: Jun. 15, 2021

(54) HYDRODYNAMIC TREADMILL: A TRACKING DEVICE TO STUDY BIOTIC/ABIOTIC SYSTEMS IN GRAVITATIONAL AND HYDRODYNAMIC FIELDS

(71) Applicant: The Board of Trustees of the Leland Stanford Junior University, Palo Alto, CA (US)

(72) Inventors: Manu Prakash, San Francisco, CA (US); Deepak Krishnamurthy, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 284 days.

(21) Appl. No.: 16/021,988

(22) Filed: Jun. 28, 2018

(65) Prior Publication Data
US 2019/0000044 A1 Jan. 3, 2019

Related U.S. Application Data

(60) Provisional application No. 62/525,955, filed on Jun. 28, 2017.

(51) Int. Cl.
| | |
|---|---|
| *A01K 29/00* | (2006.01) |
| *G01N 21/01* | (2006.01) |
| *G01N 33/483* | (2006.01) |
| *G01N 15/00* | (2006.01) |

(52) U.S. Cl.
CPC ........... *A01K 29/005* (2013.01); *G01N 15/00* (2013.01); *G01N 21/01* (2013.01); *G01N 33/483* (2013.01)

(58) Field of Classification Search
CPC ...... A01K 29/005; G01N 15/00; G01N 21/01; G01N 33/483; G01N 2015/1415; G01N 2015/1075; G01N 15/04; G01N 2015/0065; G01N 2015/1445; G01N 15/1468
See application file for complete search history.

(56) References Cited

U.S. PATENT DOCUMENTS

| | | |
|---|---|---|
| 6,876,474 B2 | 4/2005 | Kreuzer et al. |
| 7,498,551 B2 | 3/2009 | Werner et al. |
| 8,791,985 B2 | 7/2014 | Grier et al. |

OTHER PUBLICATIONS

Zhu et al., "Study of cell seeding on porous poly (D,L lactic co glycolic acid) sponge and growth in a Couette Taylor bioreactor", Dec. 3, 2009; Published in Chemical Engineering Science, vol. 65, pp. 2108-2117 (Year: 2009).*

(Continued)

*Primary Examiner* — Herbert K Roberts
*Assistant Examiner* — John M Royston
(74) *Attorney, Agent, or Firm* — Lumen Patent Firm

(57) ABSTRACT

An annular fluid-filled sample chamber is used to provide observation of unbounded motion of objects in the fluid. Rotation of the sample chamber is under automatic control to compensate for azimuthal motion of the object, thereby keeping the object in a fixed field of view of an optical observation system. Further motion control can be provided in the radial and focus directions, which can be used to provide full 3D tracking of objects as they move in the fluid. An important application of this work is to observation and tracking of objects that move up or down in the fluid with respect to gravity.

17 Claims, 15 Drawing Sheets

(56) References Cited

OTHER PUBLICATIONS

Haut et al., "Hydrodynamics and mass transfer in a Couette Taylor bioreactor for the culture of animal cells", 2003, Published in Chemical Engineering Science, vol. 58, pp. 777-784 (Year: 2003).*

* cited by examiner

HYDRODYNAMIC TREADMILL: A TRACKING DEVICE TO STUDY BIOTIC/ABIOTIC SYSTEMS IN GRAVITATIONAL AND HYDRODYNAMIC FIELDS

CROSS REFERENCE TO RELATED APPLICATIONS

This application claims the benefit of U.S. Provisional Patent Application 62/525,955 filed Jun. 28, 2017, which is incorporated herein by reference in its entirety.

FIELD OF THE INVENTION

This invention relates to observation and tracking of moving objects in a fluid.

BACKGROUND

Several natural and man-made phenomena bridge vast scales in length and time. For instance, the largest daily bio-mass migration on the planet is vast numbers of microscale plankton migrating vertically over hundreds of meters in the world's oceans; moving up and down based on circadian rhythms, sunlight or complex behavioral cues such as nutrient sources. These migrations underlie the fundamental ecological processes of the ocean, have a direct impact on the ocean's carbon cycle, and are therefore intricately tied to the planet's global carbon cycle. Solving the problem of studying such micro-scale objects over macro-scale length and time scales is currently a fundamental experimental challenge.

Observation of such motion with conventional approaches is difficult and has significant disadvantages. For example, vertical motion of particles or organisms in a laboratory test column can be tracked by a system which moves an optical sensor up and down the column according to the motion of the particle being observed. However, such a test column is undesirably large and cannot reasonably accommodate the full range of expected motion. Such an optical tracking systems is also undesirably complicated and expensive.

SUMMARY

We address the above-identified problems by providing a hydrodynamic treadmill that effectively provides unlimited scope for vertical motion. In an exemplary embodiment, a water-filled wheel with a horizontal axle provides such a treadmill, where rotation of the wheel provides vertical motion of the water that compensates the motion of the particle or organism being observed, thereby keeping it within the field of view of an optical system disposed at a fixed location. In this manner, the above described difficulties with conventional observation approaches are avoided.

This work provides a methodology/tool to track and observe micro/mesoscale (1 µm to 1 mm) biotic and abiotic systems under the influence of a gravitational field and hydrodynamic forces. The main purpose of this work is that it enables observations to be made over long time (tens of hours to days or months) and length scales (hundreds of meters) which have been hitherto not possible given the practical challenges of bridging the vast difference in scales between the observed entity (small scale) and the observation volume. Representative example systems include oceanic microorganisms, marine snow, microscopic particles such as drops falling undergoing sedimentation in air or water.

Additionally, this device also makes possible study of uniform flow past micro/mesoscale objects of non-neutral buoyancy (objects that rise/sink in an ambient fluid). Studying uniform flow past different kinds of objects such as spheres, drops, cylinders etc., is a foundational experimental tool in the fields of fluid mechanics and transport phenomena. Traditionally this is achieved using a wind or water tunnel wherein a uniform flow is maintained in a certain test section. However, fundamental limitations of fluid mechanics impose a certain minimum limit on the size of this test section which is around a meter. This also imposes a limitation on the minimum size of objects that can be studied within this test section due to fundamental limitations of high numerical aperture optical systems. This means that it is typically challenging to study uniform flow past objects which are less than a millimeter in size.

This device offers a solution to these problems using an implementation of a circular boundary-less geometry. With this approach one can lower this fundamental size limit to study uniform flow past objects which are 10-100 micrometers or lower in size. This makes possible the study of a whole class of fundamental fluid mechanics and transport phenomena which have been hitherto impossible to observe.

This work provides significant advantages compared to conventional approaches. Currently long-time tracking of particles/organisms which migrate over distances much greater than their size is limited by experimental techniques. For instance, state-of-the-art studies of vertical migrations in marine organisms use a tall vertical column and capture trajectories which are of order the field-of-view of the imaging setup (centimeters). Other studies use tall water columns with an optical system that moves vertically to track individual organisms. However, these two are limited to columns of size around hundreds of centimeters since it is infeasible to build taller columns in typical laboratory settings. Importantly these methods are bulky and expensive on account of the elaborate systems that need to be in place to translate optical systems over large distances. Studies of sedimenting or rising particles and drops suffer from similar limitations.

By implementing a circular stage, this work avoids many of the challenges of previous methodologies. The system can be compact (20 cm in size) and may be integrated seamlessly with conventional microscopes as a replacement tracking stage, yet allows motions of hundreds of meters to be observed, a scale of observation that has been hitherto impossible.

Numerous applications are enabled by this technology. For example, long-time tracking and microscopy of marine microorganisms is important for marine ecology, biological oceanography, physical oceanography and is specifically applicable to phytoplankton, zooplankton, larvae of marine organisms, and marine snow dynamics. Observing sedimenting microparticles and microdroplets is important in atmospheric sciences and is specifically applicable to cloud formation, rain drop coalescence mechanisms, and aerosol particle dynamics. Observing growth of microcrystals in a fluid is important for materials science and is specifically applicable to understanding the role of fluid flow on crystal structure. Observing three-dimensional fluid flow is important for fluid mechanics and is specifically applicable to mapping the three-dimensional flow around an object moving under the combined influence of gravity and/or its own motility.

DETAILED DESCRIPTION

In general terms, this work provides a boundary-less, fluid-filled geometry and closed-loop image processing and tracking to observe biotic and abiotic systems whose motions have a significant vertical component owing to the effects of gravity, hydrodynamics and active motility. A circular geometry, which is implemented as a wheel with a fluid-filled annulus, effectively makes one of the dimensions periodic and boundary-less, meaning that the particle or organism under observation can freely move in that direction without being hindered by a wall (see FIG. 1 below). To enable long-time observation, a closed-loop tracking method is implemented such that when the object moves with respect to the fluid, in a net vertical direction, the wheel moves in the opposite sense so that the object is kept within the field-of-view at all times. For small particles or organisms of interest here this angular motion is well-approximated as a linear motion and the dynamics are unaffected by the tracking motions of the wheel. Tracking in the two other orthogonal directions can be implemented using linear motion on top of this long-time tracking along the vertical direction using angular motion.

Figure 1:
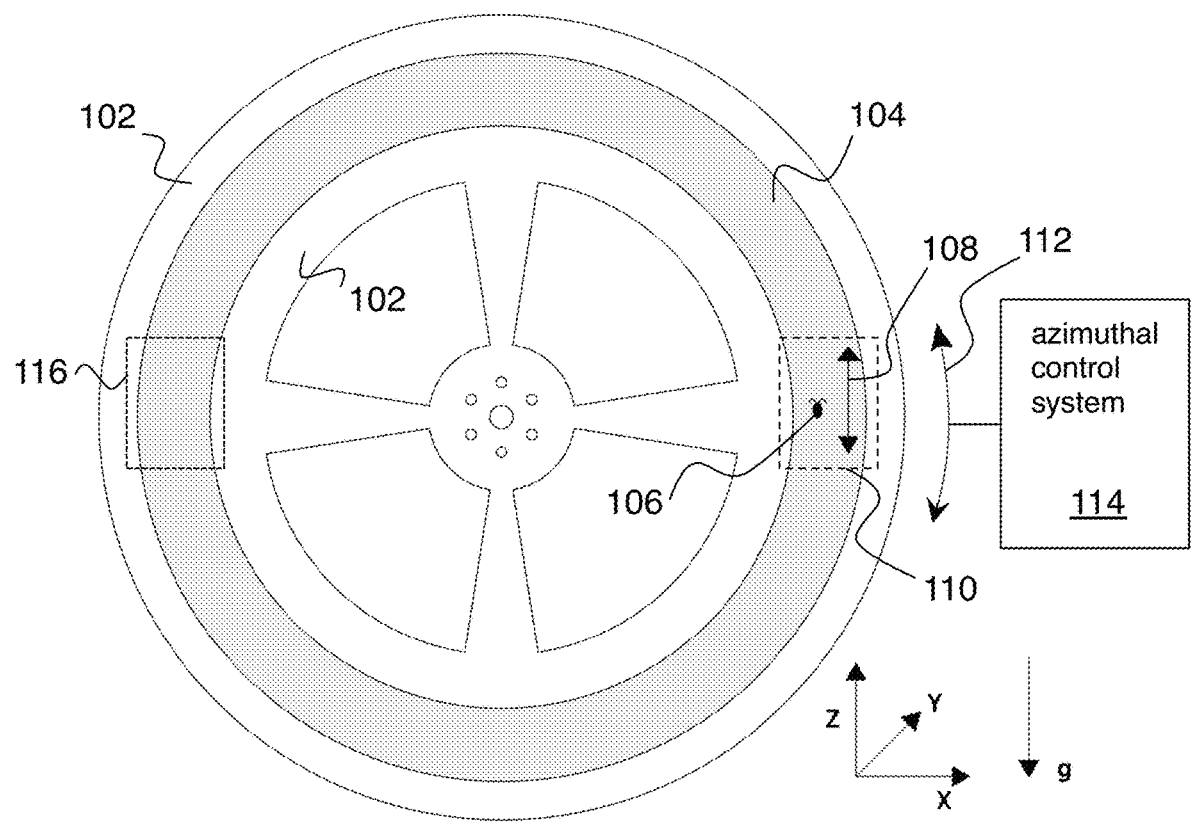
FIG. 1 shows an embodiment of the invention.

FIG. 1 shows an exemplary embodiment of the invention, which is an apparatus for observing unbounded motion of an object 106 in a fluid 104. Here an optically transparent sample chamber 102 is configured as an annulus filled with fluid 104. An azimuthal control system 114 is configured to rotate sample chamber 102 to compensate for azimuthal motion 108 of object 106 in fluid 104 such that object 106 continuously remains visible within a predetermined field of view 110. Here arrows 112 schematically show the rotation of sample chamber 102 provided by azimuthal control system 114. For brevity of description, sample chamber 102 is often referred to as a wheel in this description. The azimuthal motion control can be carried out by a fine stepper motor/rotational stage that applies rotational movements to the wheel.

Although this basic idea of motion compensation can be applied to an object 106 located in any part of the wheel, an important special case is when azimuthal motion of object 106 is substantially up or down with respect to an ambient gravitational field, as shown on FIG. 1. Here the rotation axis of the wheel is horizontal, and as a result azimuthal motion of object 106 in field of view 110 is substantially up or down with respect to the ambient gravitational field g, as shown. Field of view 116 also has this property, which can be summed up as these fields of view being at 3 o'clock and 9 o'clock positions on the wheel. This idea can be extended to compensate for any external bias field capable of inducing anisotropic motion of the object directly (e.g., abiotic particle falling through a fluid) or indirectly (e.g., a biological organism swimming up or down with respect to gravity). The direction along the bias field is made boundary-less by implementing an annular fluidic geometry and choosing the field of view appropriately. Movements of the object in the direction of the bias field are compensated by rotational movements of the wheel. Here azimuthal motion of the object is defined as motion of the object around the circle of the sample chamber. In laboratory coordinates, this can be thought of as being tangential motion (z directed motion on the figures, for the field of view as shown). The time duration of object tracking is unlimited in principle, e.g., from milliseconds to a month. Object 106 is unrestricted in its vertical motion, enabling long tracks (up to hundreds of meters) to be observed.

The tracking procedure ensures that the object can undergo large relative displacements in the direction of the potential field while being stationary (in the potential field dimension) in the lab reference frame. The device ensures that the object can be imaged at high spatial and temporal resolution since the optical setup need not move to track the object.

The wheel preferably has an inlet and outlet port to fill and drain fluid from the wheel. The material used to fabricate the wheel is chosen to be optically clear in the plane of the wheel. The field of view where the object of interest is tracked is preferably 90 degrees from the vertical symmetry axis of the wheel (e.g., 110 and 116 on FIG. 1). The inner and outer rims of the annulus are preferably made from materials with high thermal inertia to stabilize thermal flows in the fluid inside the wheel.

This approach can be used to track the motion of any kind of object in a fluid. Such objects include, but are not limited to: biotic objects, abiotic objects, neutrally buoyant objects, non-neutrally buoyant objects, and objects having a size of 1 mm or less.

Exemplary values and ranges for system parameters are as follows. In general, practice of the invention does not depend critically on any of these variations. The object size can be from 100 nm-5 mm. Smaller or larger objects require a suitable change in the optical assembly as well as the dimensions of the wheel. The wheel diameter can be from 10 cm-50 cm. Larger wheel diameters allow a closer approximation of the motion to linear motion. Smaller wheel diameters are suitable for more portable applications. The angular velocity range of the wheel can be from 100 μrad/s-0.1 rad/s. This range depends on the slowest and fastest motions that need to be tracked by the wheel. This obeys $\omega = v/R$, where $\omega$ is the angular velocity, R is the wheel radius and the v is the minimum (or maximum) linear velocity of the object. The fluid viscosity can be about 0.001 Pa s (the viscosity of water). Water is the most typical fluid for biological measurements, however the operating principles of the device would remain unchanged for other viscous fluids. The fluid density can be 1000 kg/m^3 (water), Other lighter or denser fluids can also be used based on the application. Fluid density can be modulated to change the relative velocity between a sedimenting object and the fluid. This is an important parameter to change the particle Reynolds number in fluid mechanics studies.

Figure 2:
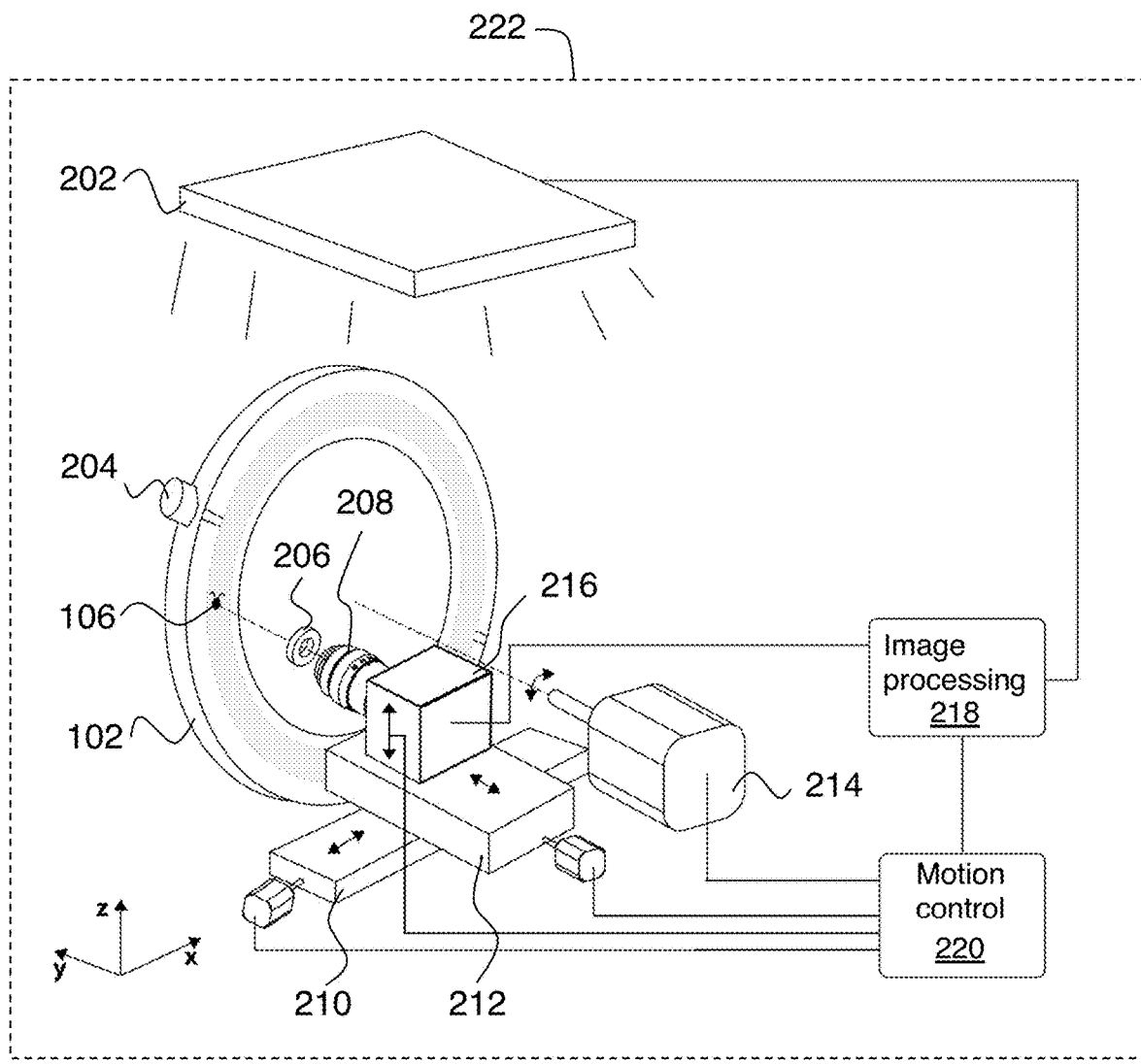
FIG. 2 shows another embodiment of the invention.

In preferred implementations of the concept of FIG. 1, an optical observation system disposed to observe the predetermined field of view is typically used. FIG. 2 shows an example of this approach, along with several optional features of preferred embodiments. These optional features can be practiced individually or in any combination. Here 202 is ambient light control, 204 is an inlet for an onboard pump, 206 is a liquid lens or fast actuator for rapidly changing the focal plane of the optical system (as discussed below in connection with FIGS. 3A-D), 208 is a microscope objective, 210 is a linear actuator for radial motion control (x direction on FIG. 2), 212 is a linear actuator for focus control (y direction on FIG. 2), 214 is an actuator for rotating sample chamber 102, 216 is a camera (optionally including a z-directed actuator as shown), 218 is an image processing system connected to camera 216 and light 202, and 220 is motion controller connected to actuators 210, 212, 214 and to any actuator that may be present in camera 216. Optionally, the entire assembly is surrounded by a thermal enclosure (which may or may not be under active temperature control) within which the sample chamber and the optical observation system are enclosed. This serves the dual purpose of reducing thermally driven flows in the annular fluid and also allowing controlled illumination. The radial motion control and the focus motion control can be any combination of open-loop control and closed-loop control.

In this example, radial motion control and focus motion control of a relative position of the sample chamber and the optical observation system are provided. The tracking movement along the X and Y directions can be carried out by linear actuators which move the optical assembly. FIG. 11 shows an alternative configuration where these actuators move the sample chamber instead of the optical assembly.

Further details of preferred embodiments include the following. The object can be imaged using an optical unit having a suitable combination of lenses based on the optical resolution desired and the object being observed. The optical unit can be modular and can be easily swapped out to image objects of different sizes (microns to mm) and at different optical resolutions. The images can be collected using a camera and processed using an image processing unit (in particular a computer CPU or GPU).

As shown on FIG. 2, there are two ways to compensate for z-directed motion of object 106—rotating sample chamber 102 via actuator 214 and z-positioning of camera 216. For now it will be convenient to refer to these both as z-tracking, and the differences will be considered in greater detail below.

The images from the camera can be processed to extract the location of the object. Command signals can be sent from the image processing unit 218 to the motion control unit 220 which moves the Z, X and Y stages to compensate for the object's motion. Tracking along the Z and X directions can be performed using the object position as extracted from the 2D image. Tracking along the Y direction (optical axis) can be carried out using a method detailed below.

The benefits of the circular, periodic geometry of the fluid in the annulus comes with the caveat that there is a small delay between the motion of the wheel and the motion of the fluid itself. This results from the inertial delay in the transfer of momentum. This time poses a natural restriction on the speed and acceleration of objects that can be tracked using just the wheel alone. Note that the operational limits of the device even with such a restriction is quite broad.

We provide a solution to overcome such restrictions due to this inertial delay in the form of a load-sharing based tracking approach. Briefly, the tracking in the Z-direction (direction of the potential field) is carried out by both the wheel (via actuator 214 on FIG. 2) as well as a smaller linear actuator that couples to the optics assembly (216 on FIG. 2). The smaller linear actuator handles the high frequency (e.g., 10-100 Hz) movements of the object while the wheel handles the lower frequency (e.g., 0-10 Hz) movements of the object. This allows objects which have a high-frequency movement to be studied over long length and time-scales without modifying the behavior due to the tracking. This amounts to providing translational motion control of the relative position of the sample chamber and the optical observation system, where the translational motion control and the azimuthal motion control both act to compensate for azimuthal motion of the object. Preferably the frequency range for the azimuthal motion control is from 0-10 Hz. Preferably the frequency range for the translational motion control is from 10-100 Hz.

Figure 3A:
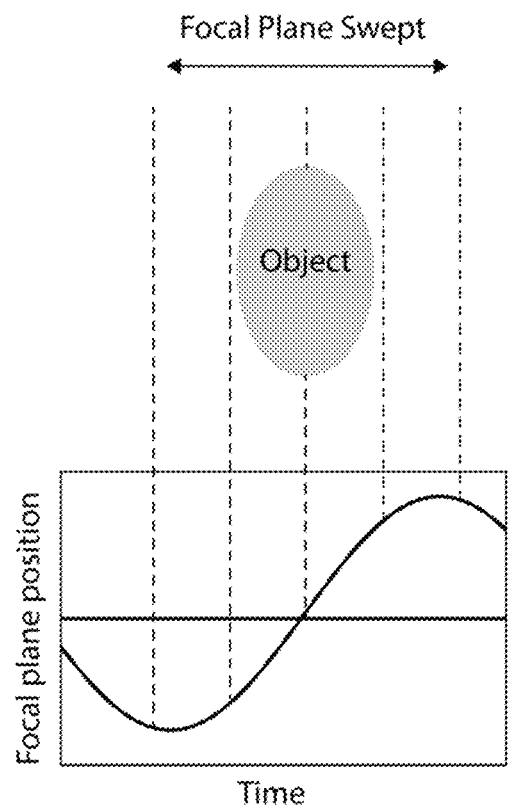
FIGS. 3A-D show operation of focus control in connection with embodiments of the invention.
Figure 3B:
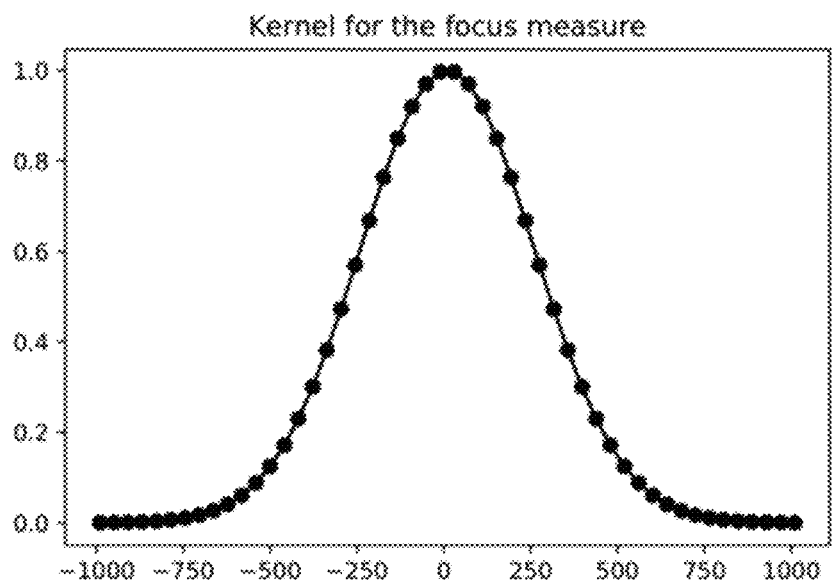
Figure 3C:
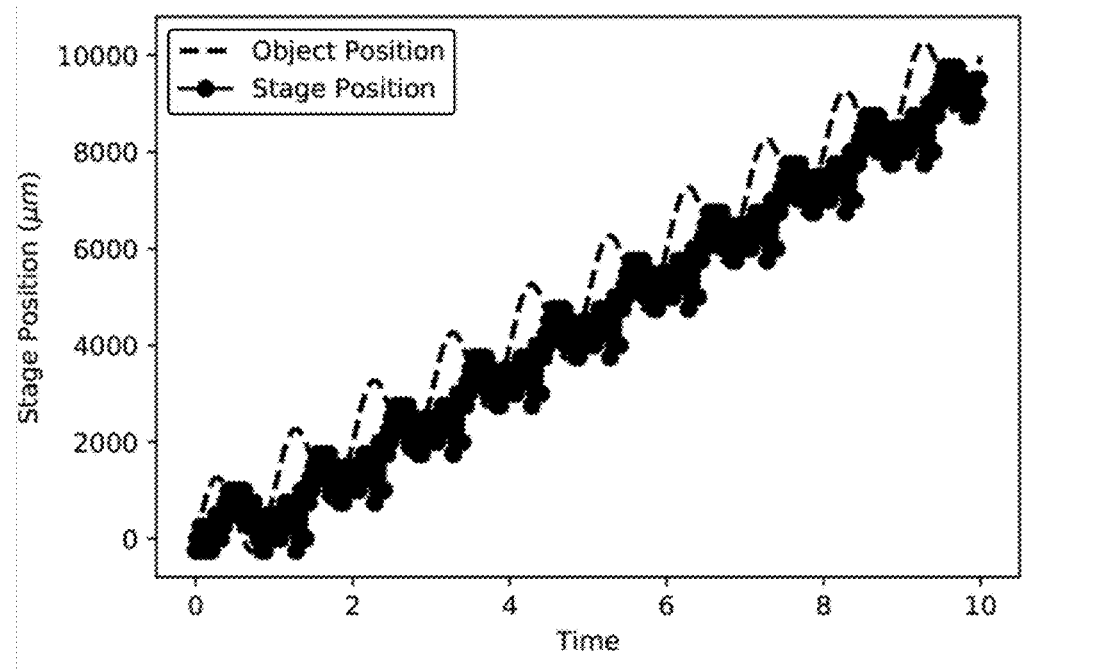
Figure 3D:
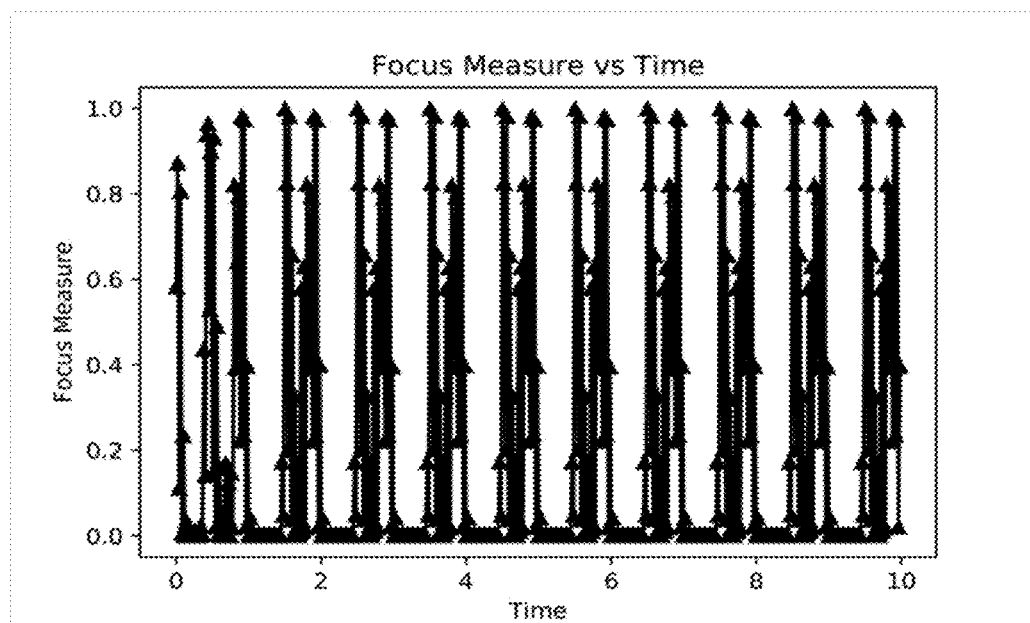

A key part of this approach is that it allows objects to be tracked over long time scales. This requires that the object be maintained in focus, this is information which cannot be extracted from a single 2D image from the camera. FIG. 3A shows a schematic of a preferred focus-tracking method, where the focal plane of the imaging system is scanned rapidly to capture a series of images at different focal planes. A fast actuator or liquid lens (206 on FIG. 2) is used to rapidly modulate the focal plane of the optical system. A focus-metric is calculated in real-time and the stage is offset to the location that maximizes this metric. A gradient climbing algorithm can be used to estimate the focal depth corresponding to the local maxima of this metric. The Y-stage is offset by the amount which is the error between the current position and the focal depth calculated in the previous step. FIG. 3B shows an exemplary fall-off of the focal metric as the focal plane moves away from the object position. FIG. 3C is a numerical simulation showing the focus-tracking method in action. The dashed curve represents the simulated trajectory of the object, and the symbols represents the position of the stage as it tracks the object. FIG. 3D is a plot of the focus-measure as a function of time which is used by the algorithm to estimate the object position.

In other words, the focus motion control is based on scanning a focal plane of the optical observation system in a focus range and adjusting the relative position of the sample chamber and the optical observation system such that the object is in best focus at a predetermined point of the focus range as the object moves.

Figure 4A:
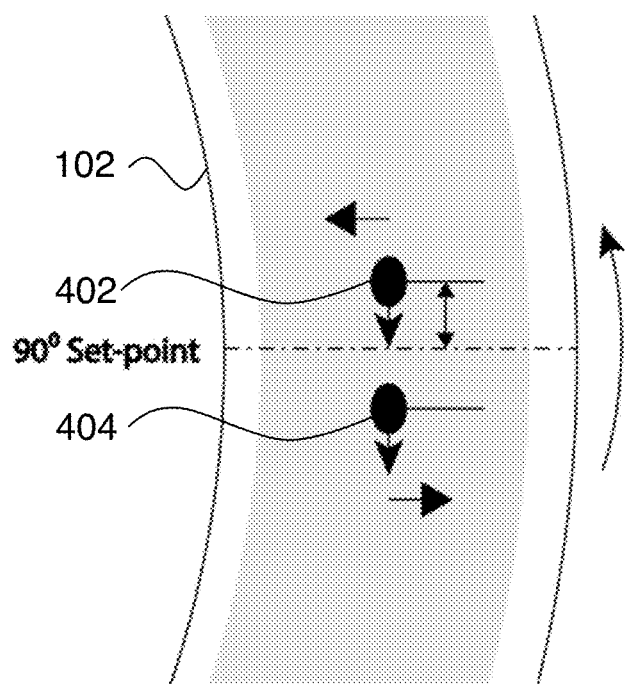
FIGS. 4A-B show control of radial position of the object and of object orientation.

The circular geometry of the fluidic chamber allows for a simple way to manipulate the radial position (FIG. 4A) and the orientation (FIG. 4B) of an object in the fluid. More explicitly, FIG. 4A shows how a set-point for the azimuthal position of the object can be selected to cause the object to move radially within the sample chamber due to the ambient gravitational field, whereby both azimuthal and radial control of object position is provided. For example, if the object is moving down on FIG. 4A, then having a set point 402 above the 90 degree dashed line will cause the object to move inward radially. Similarly, having a set point 404 below the 90 degree dashed line will cause the object to move outward radially. If the object were moving upward on FIG. 4A, then set points 402 and 404 would have outward and inward radial motion, respectively.

Figure 4B:
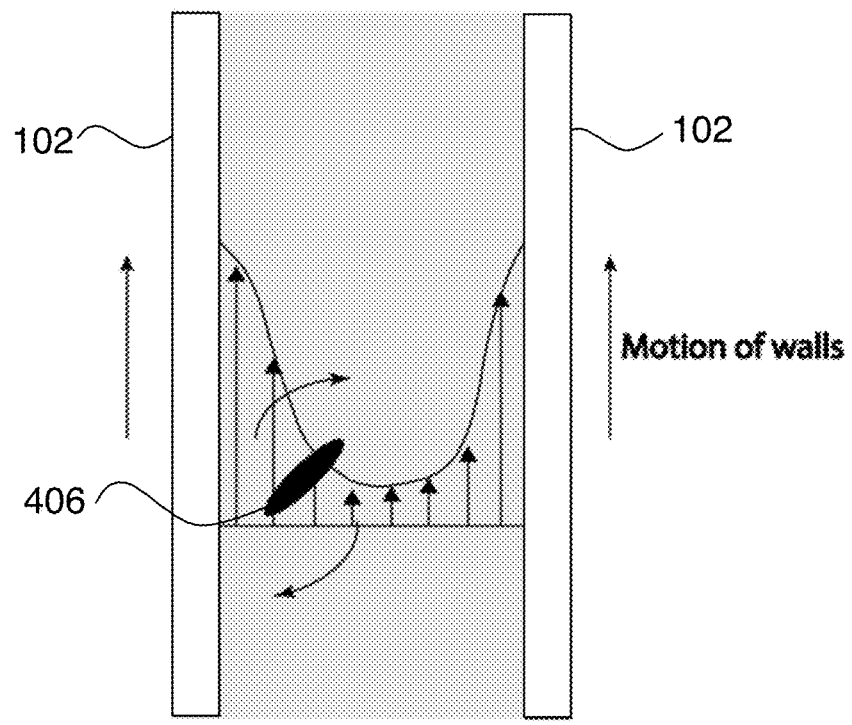

FIG. 4B schematically shows how the orientation of the object can be changed by generating shear in the fluid via angular acceleration of the sample chamber. As shown on the figure, such acceleration of the sample chamber can lead to a non-uniform fluid velocity profile within the sample chamber, which can act to rotate object 406 as shown. For a given object size and shape, the orientational trajectory can be known analytically hence allowing one to flip objects in a controlled manner.

Figure 5:
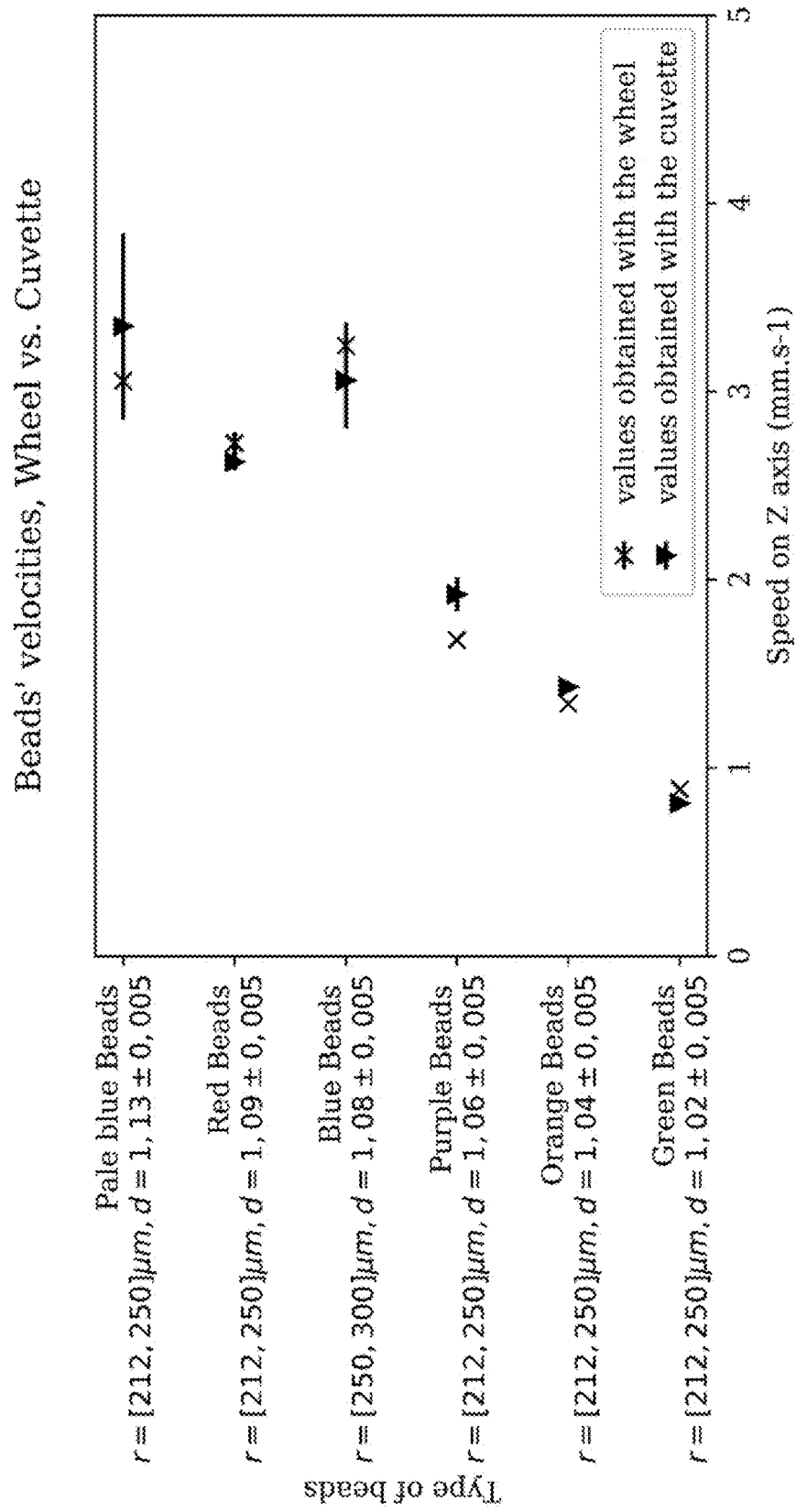
FIG. 5 is a comparison of results of the present work with a conventional measurement technique for velocities of beads falling through a fluid.

FIG. 5 shows results of a test of this approach. The working principle was tested by measuring the sedimentation speed of Density Marker Beads (Cospheric Inc.) of precisely calibrated density using the device to track the beads. Note that in this experiment the beads are stationary in the lab reference frame since the device applies a counter rotation that exactly balances the sedimentation rate. As a control experiment the same beads were tracked while they sediment in a tall cuvette past a fixed optical setup. In this case the beads are not stationary in the lab reference frame and the sedimentation speed is obtained by image processing to calculate the bead position as a function of time. The plot shows the results from both these experiments compared along with the theoretical predictions (mean: symbols, one standard deviation range: solid lines). This comparison shows that the device accurately measures the sedimentation speed and is able to distinguish even small variations in density of around 0.02 g/cc.

Figure 6A:
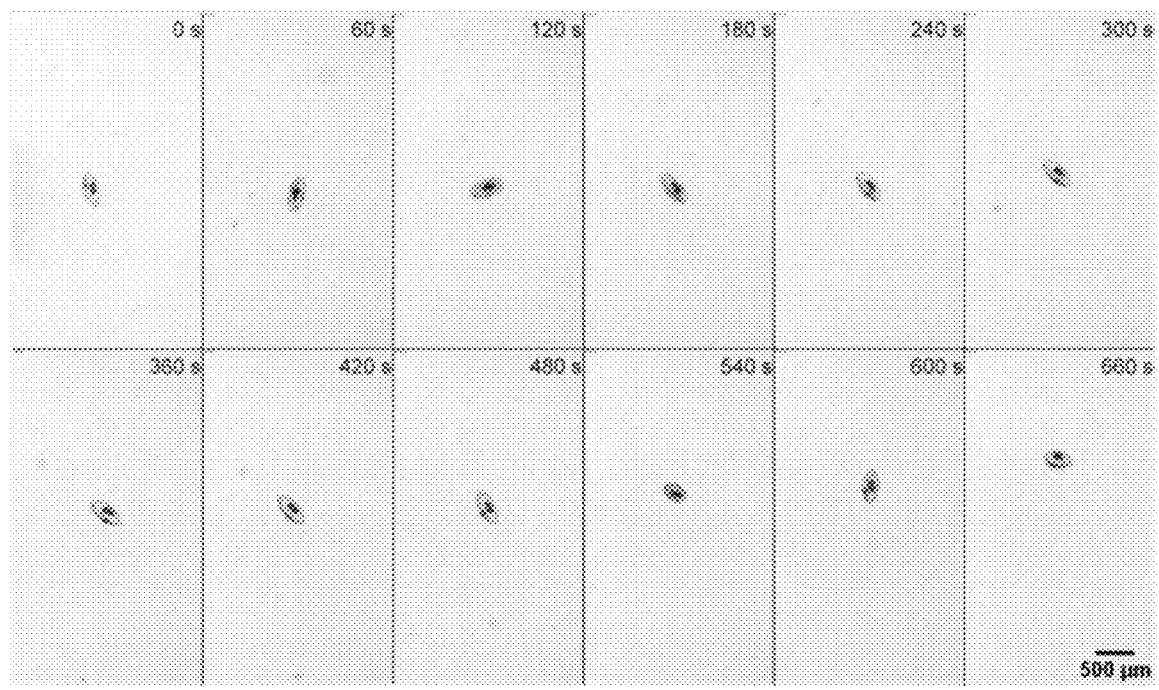
FIGS. 6A-B show tracking results as obtained from an embodiment of the invention.
Figure 6B:
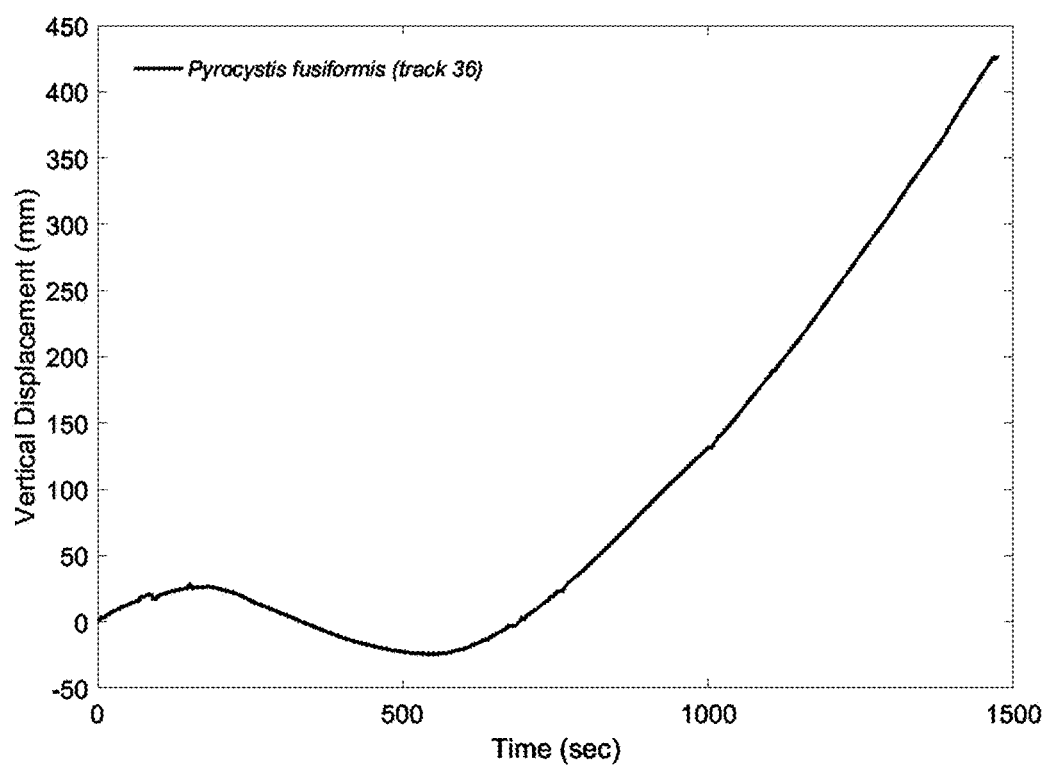

FIGS. 6A-B show tracking of *Pyrocystis fusiformis*. Vertical migration data for *Pyrocystis fusiformis*, a common marine dinoflagellate, were recorded using this approach. FIG. 6A shows a series of snapshots spaced apart by a minute of the organism as it migrates vertically. FIG. 6B is a plot of vertical displacement of *Pyrocystis fusiformis* as a function of time.

Figure 7A:
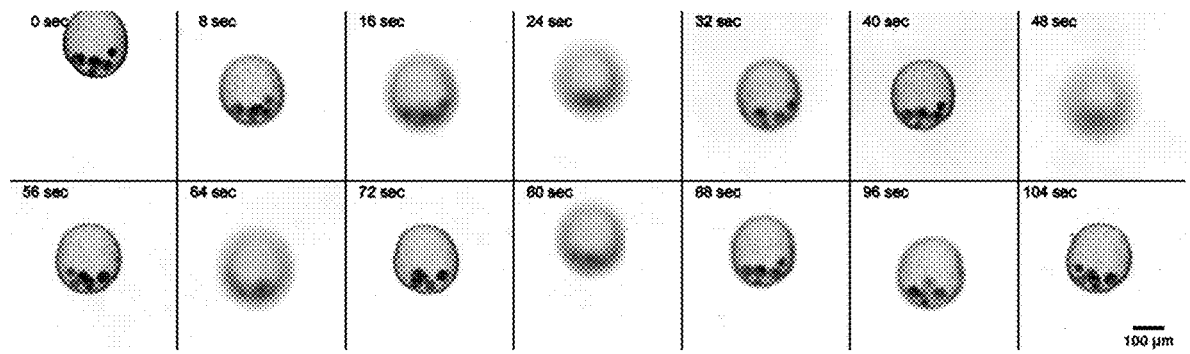
FIGS. 7A-B show further tracking results as obtained from an embodiment of the invention.
Figure 7B:
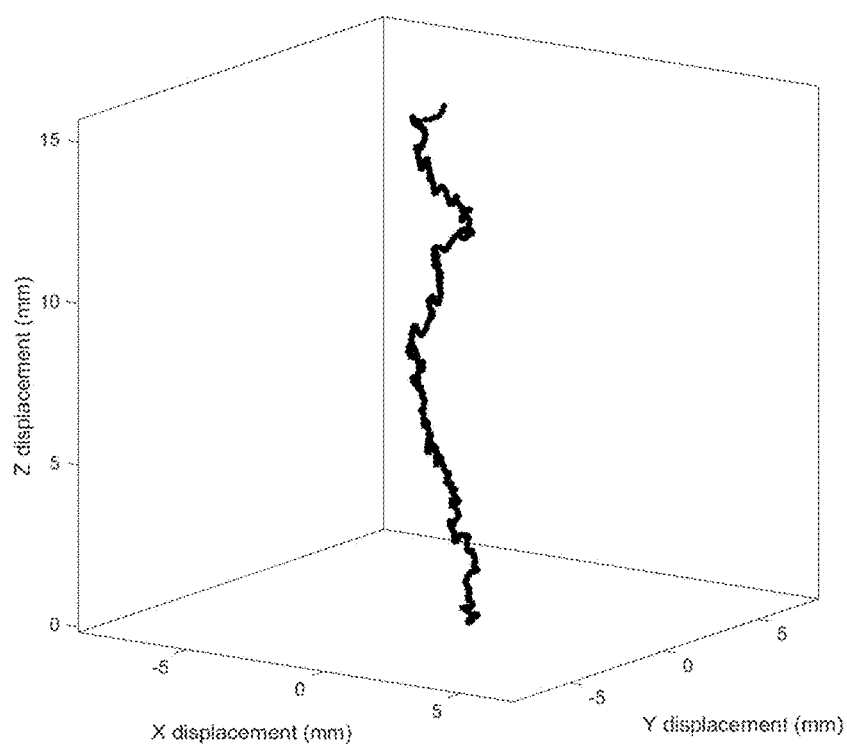

FIGS. 7A-B show tracking of *Volovox aureus*, a common freshwater colonial algae, recorded using this approach. FIG. 7A shows a series of snapshots spaced apart 2 seconds of the organism as it migrates vertically and also rotates about its body axis. Note that microscopic details such as the daughter colonies within the main colony are clearly visible. FIG. 7B shows a 3D track of *Volovox aureus* measured using this approach. Thus the radial motion control, the focus motion control and the azimuthal motion control can be combined to provide a 3-D volumetric scan of motion of the object.

Figure 8A:
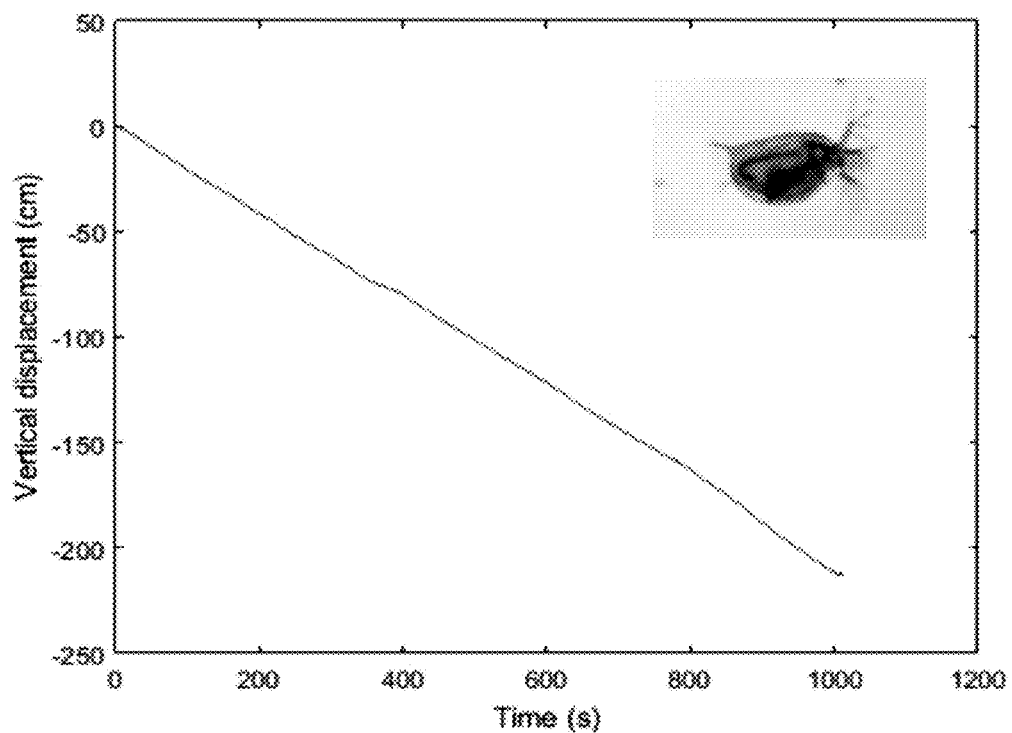
FIGS. 8A-B show further tracking results as obtained from an embodiment of the invention.
Figure 8B:
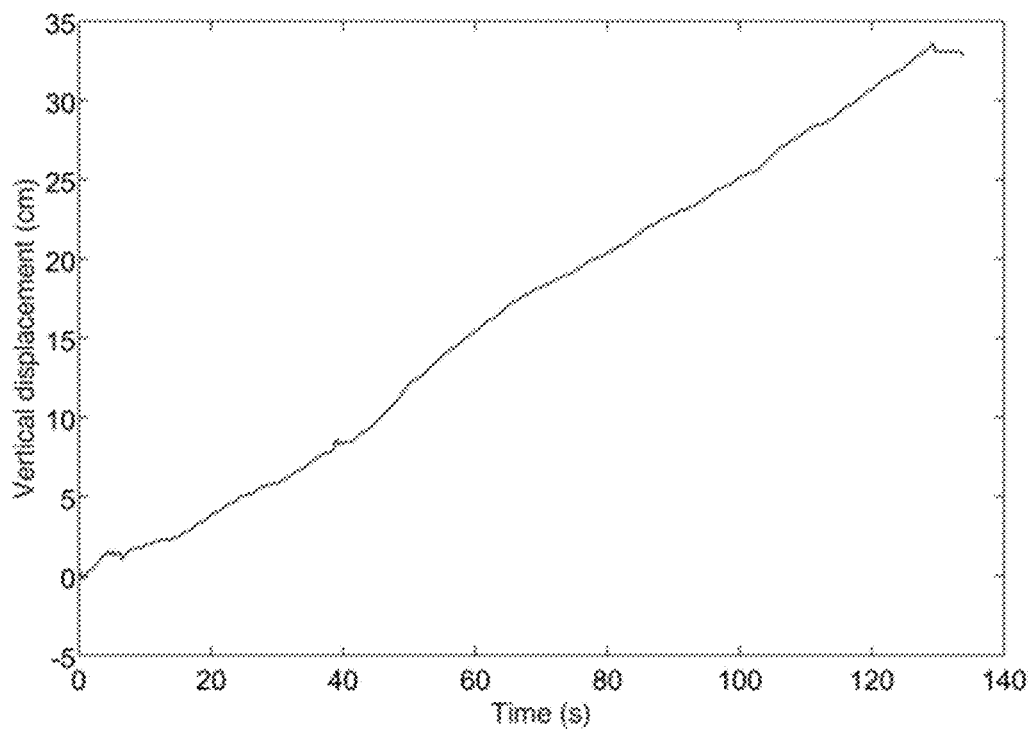

FIGS. 8A-B shows vertical migration data recorded using this approach. The plots shows the vertical displacement of *Daphnia magna*, a common freshwater organism, as a function of time. The total duration of the track is around 15 minutes in FIG. 8A during which the organism swims down more than 2 meters. In FIG. 8B the organism swims upwards against gravity. The inset in FIG. 8A shows the organism as observed with the device.

Figure 9:
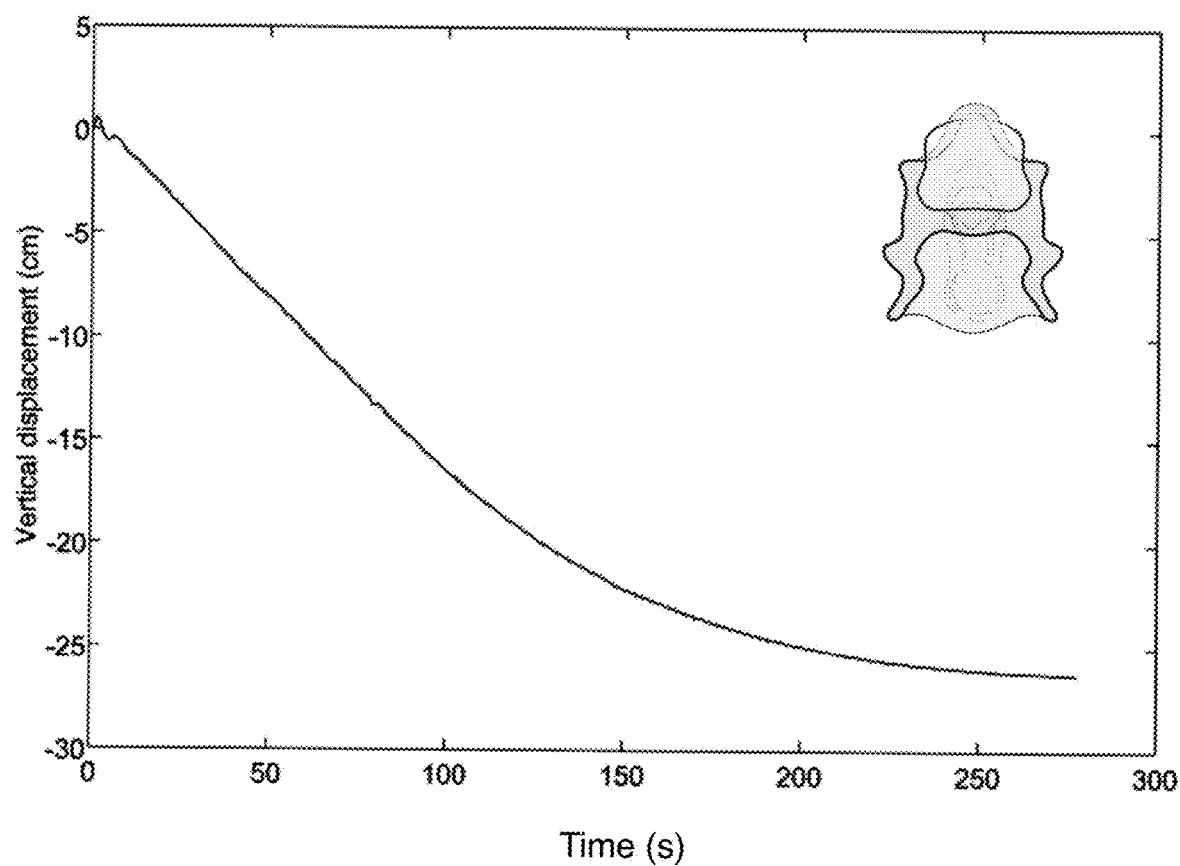
FIG. 9 shows further tracking results as obtained from an embodiment of the invention.

FIG. 9 shows vertical migration data recorded using this approach. The plot shows the vertical displacement of the larval forms of *Patiria miniata* (Starfish), a marine organism, as a function of time. The total duration of the track is around 5 minutes during which the organism swims downwards. The inset shows the organism as observed on the device.

Figure 10A:
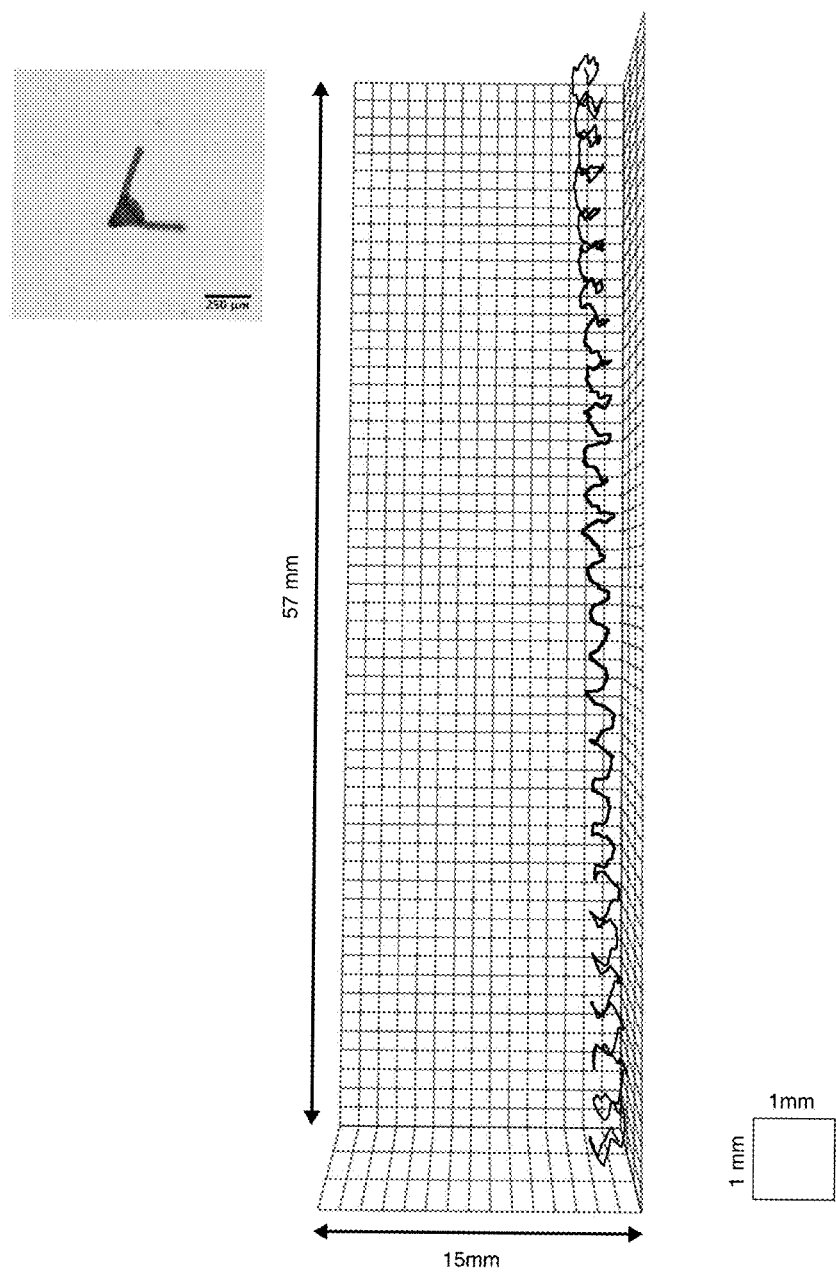
FIGS. 10A-C show further tracking results as obtained from an embodiment of the invention.
Figure 10B:
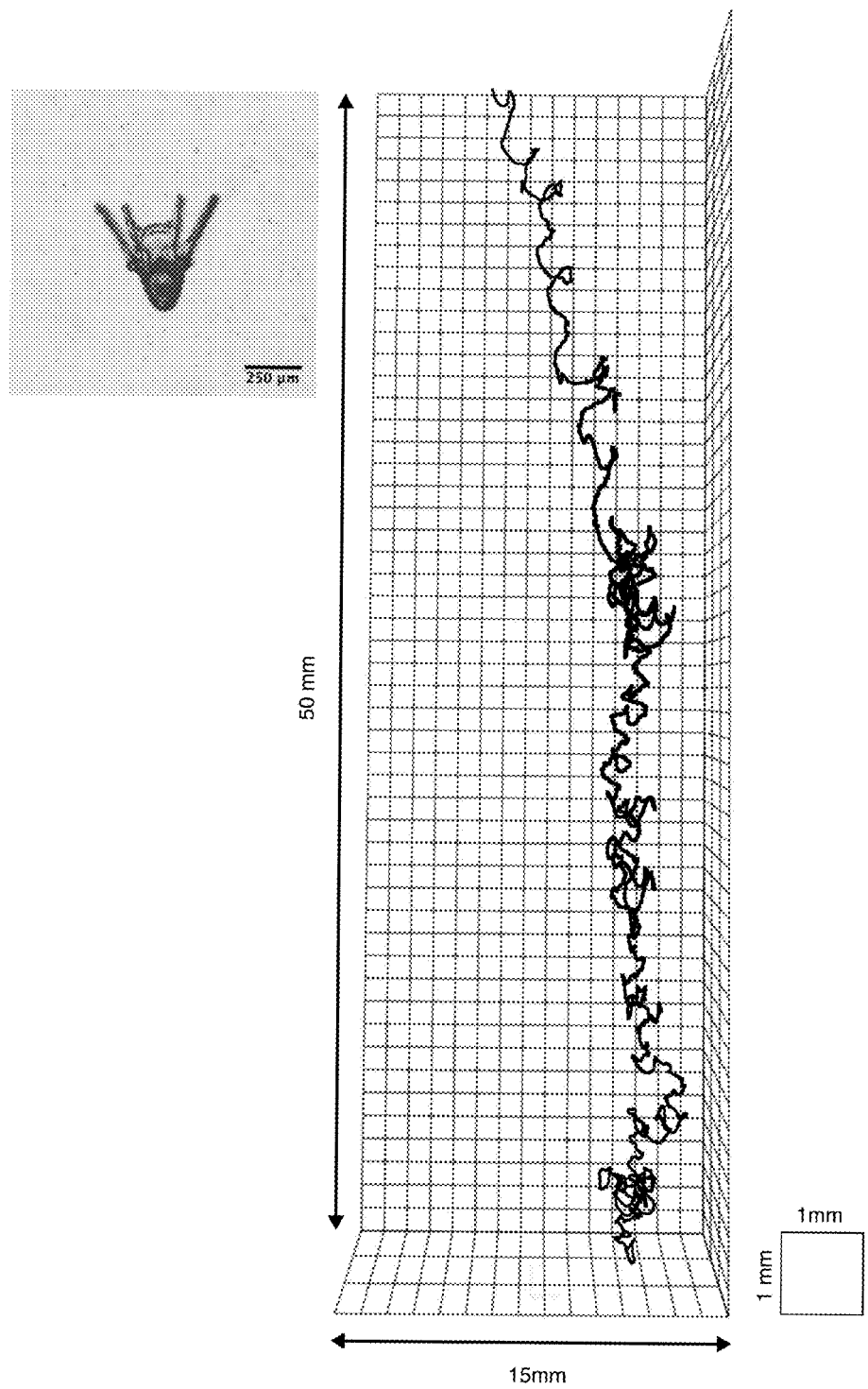
Figure 10C:
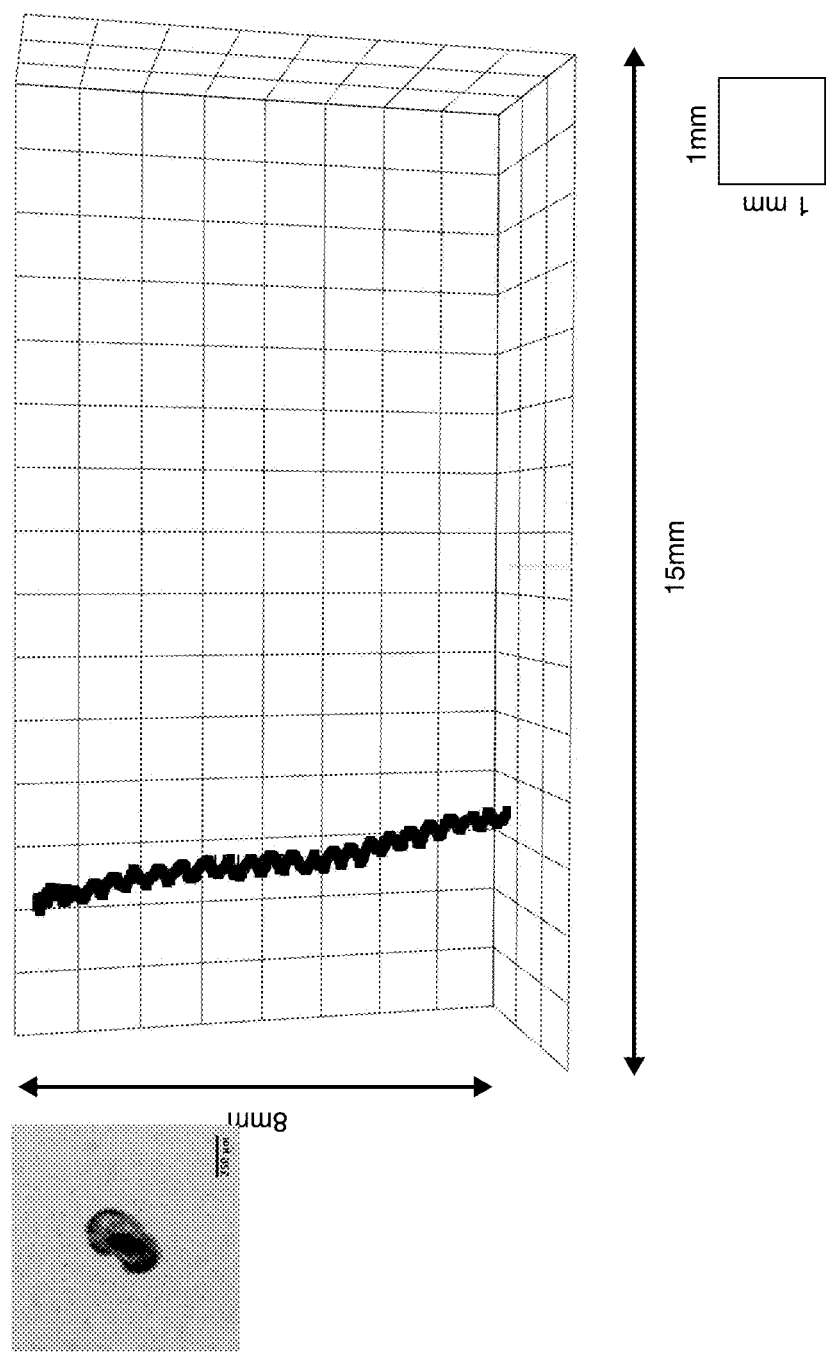

FIGS. 10A-C show 3D tracking results for freely swimming marine invertebrate larvae obtained using this approach. FIG. 10A shows results for *Ophiuroidea* (Brittle Star) larvae. FIG. 10B shows results for *D. excenricus* (Sand dollar) larvae. FIG. 10C shows results for *A. parvimensis* larvae (Sea Cucumber).

Figure 11A:
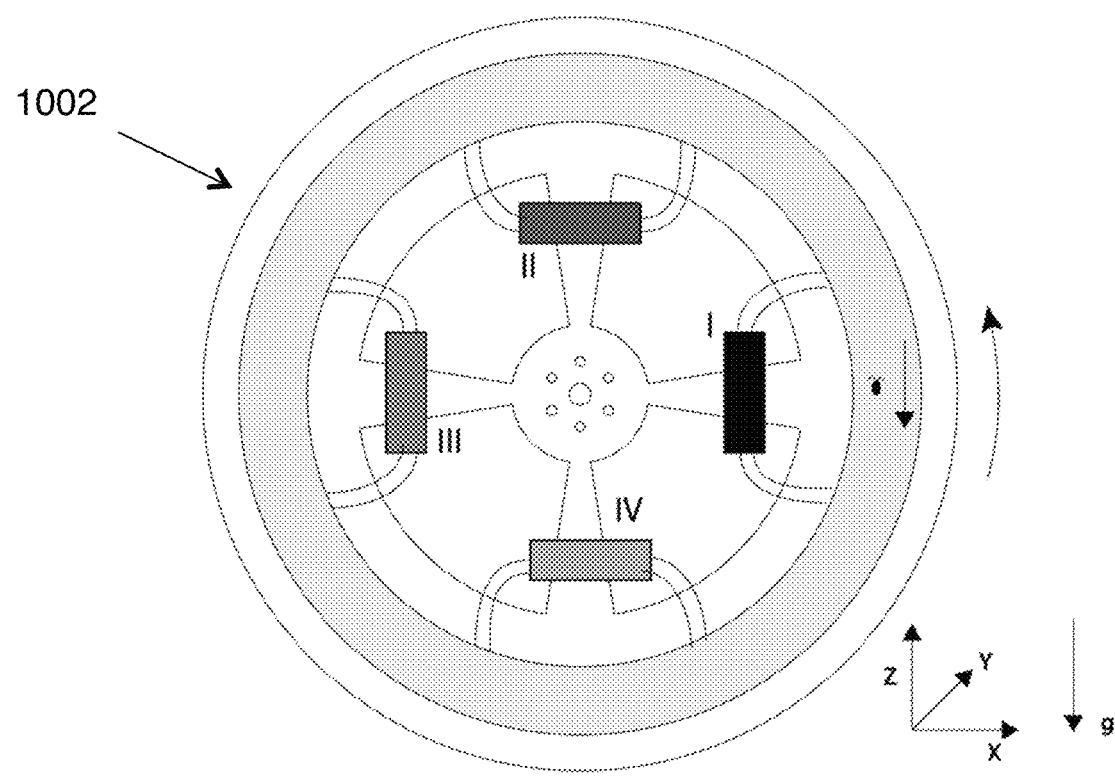
FIGS. 11A-B schematically show how chemical concentration in the sample chamber can be varied according to virtual depth.
Figure 11B:
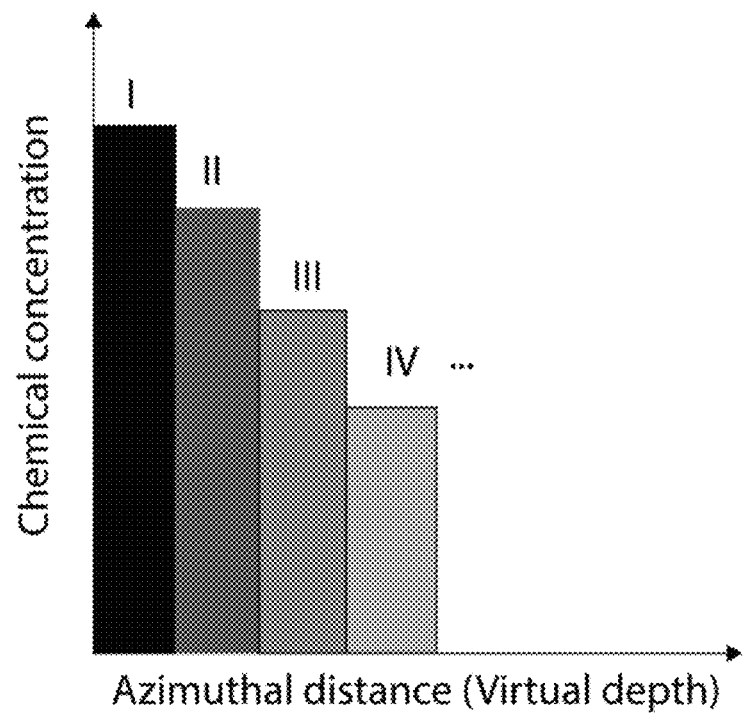

FIG. 11A is a schematic of an embodiment as used for exposing an object to a varying environmental condition such as ambient chemical concentration/temperature. Here sample chamber 1002 includes a system for varying environmental parameters of the fluid as a function of a virtual depth as the virtual depth varies according to azimuthal motion of the object. Here this system is schematically shown by reservoirs I, II, III and IV having varying chemical concentrations as shown on FIG. 11B. As the wheel rotates, the object will experience different chemical concentrations according to total vertical distance traveled.

Although an object in a hydrodynamic treadmill does not move in the laboratory coordinates, it is convenient to define virtual depth as being an artificial depth based on the total vertical distance compensation provided by the system for an object being observed in the hydrodynamic treadmill. This distance compensation is the wheel radius times the net total angle through which the wheel has rotated, accounting properly for multiples of 360 degrees. A new class of biological experiments can be performed by altering environmental parameters as this virtual depth varies. This allows for direct observation of the behavior of a biological organism (e.g., plankton) as it moves vertically through tens or even hundreds of meters, and for providing appropriate depth cues to the organism for such observation.

The environmental parameters that can vary with virtual depth can include one or more of: optical intensity, optical spectrum, optical polarization, nutrient concentration, oxygen concentration, chemical species concentration, pressure, electric field direction and intensity, and magnetic field direction and intensity. This provides modalities to study influence of slow temporal and spatial (ecologically relevant) gradients of light, chemical concentration, salinity, temperature etc.

More specifically, the following environmental parameters can be modified.

Light: Intensity, spectrum and polarization can be encoded as a function of virtual depth. As the object moves along the unbounded direction, an external light source (e.g., 202 on FIG. 2) gradually varies the illumination properties to mimic various natural environments. For instance, the change in light intensity, spectrum and polarization as an object sinks from the surface of the ocean can be simulated.

Chemical: Local variations in chemical concentration (e.g., of nutrient, oxygen, and/or odorant cues) can be introduced by using small volumes of chemicals stored on-board the wheel and released into the annular fluidic chamber at a particular virtual depth. This can be done using on-board micro-pumps to slowly modify the local chemical concentration, as schematically shown on FIG. 11A. Such a capability will be especially relevant for running behavioral assays to understand effects of various chemicals on organismic behavior.

Pressure can be modified by applying a static pressure to the fluid in the chamber whose intensity is modulated as function of virtual depth.

Electromagnetic fields: Different intensities and directions of electromagnetic fields can be applied as a function of virtual depth by suitable arrangements of devices like Helmholtz coils.

Figure 12:
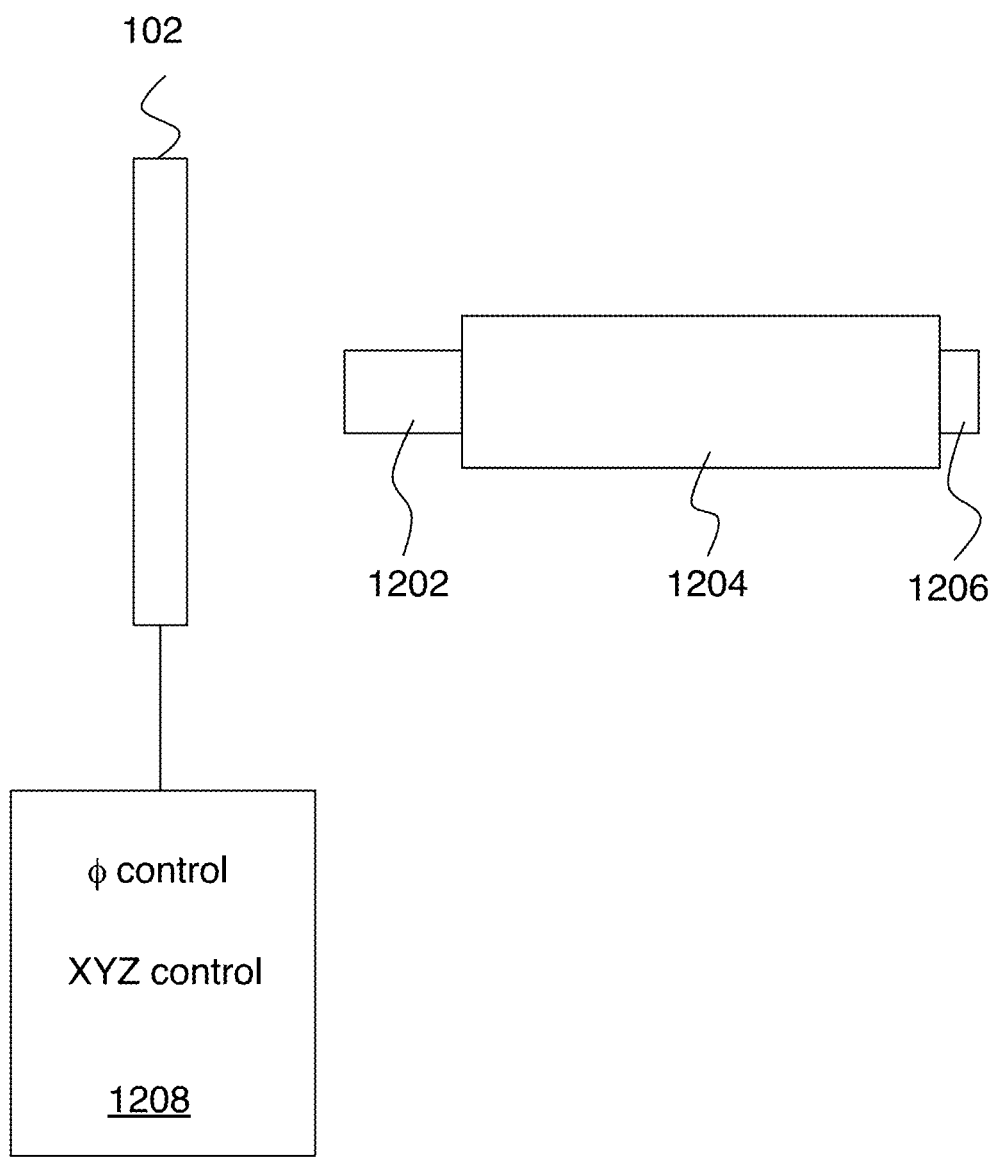
FIG. 12 shows an embodiment of the invention configured as a controllable stage for use with a conventional microscope.

In the example of FIG. 2, motion control is applied to the optical observation system, which amounts to providing a custom microscope for observing the object. The side view of FIG. 12 shows an alternative embodiment where the optical observation system is a horizontally mounted microscope (objective 1202, body 1204 and eyepiece or camera 1206), and where all control of relative position of the optical observation system and the sample chamber is provided by motion of the sample chamber via stage controller 1208. Here 102 is the rotatable sample chamber seen in a side view. This configuration is more suitable for applications where the device is used as a standalone microscope stage for retrofitting a conventional microscope.

The invention claimed is:

1. Apparatus for observing unbounded motion of an object in a fluid, the apparatus comprising:
   an optically transparent sample chamber configured as an annulus filled with a fluid and having an axis of rotation; and
   an azimuthal control system configured to rotate the sample chamber as a unit about the axis of rotation to compensate for azimuthal motion of an object in the fluid such that the object continuously remains visible within a predetermined field of view;
   wherein azimuthal motion of the object is motion of the object in a ϕ direction of an r, ϕ, z system of cylindrical coordinates having the axis of rotation of the sample chamber as its z axis.

2. The apparatus of claim 1,
   wherein a resultant gravitational field is present at a location of the apparatus; and
   wherein the apparatus is configured such that the azimuthal motion of the object is substantially up or down with respect to the resultant gravitational field.

3. The apparatus of claim 2, further comprising a system for varying environmental parameters of the fluid as a function of a virtual depth as the virtual depth varies according to azimuthal motion of the object;
   wherein the virtual depth is a radius of the sample chamber times a net total rotation angle of the sample chamber.

4. The apparatus of claim 3, wherein the environmental parameters include one or more parameters selected from the group consisting of: optical intensity, optical spectrum, optical polarization, nutrient concentration, oxygen concentration, chemical species concentration, pressure, electric field direction and intensity, and magnetic field direction and intensity.

5. The apparatus of claim 2, wherein a set-point for an azimuthal position of the object is selected to cause the object to move radially within the sample chamber due to the ambient gravitational field, whereby both azimuthal and radial control of object position is obtained.

6. The apparatus of claim 1, wherein the control system is further configured to generate shear in the fluid via angular acceleration of the sample chamber, whereby an orientation of the object can be changed.

7. The apparatus of claim 1, wherein the object is selected from the group consisting of: biotic objects, abiotic objects, neutrally buoyant objects, non-neutrally buoyant objects, and objects having a size of 1 mm or less.

8. The apparatus of claim 1 further comprising an optical observation system disposed to observe the predetermined field of view.

9. The apparatus of claim 8, further comprising radial motion control and focus motion control of a relative position of the sample chamber and the optical observation system.

10. The apparatus of claim 9, wherein the radial motion control and the focus motion control include open-loop control.

11. The apparatus of claim 9, wherein the focus motion control comprises scanning a focal plane of the optical observation system in a focus range and adjusting the relative position of the sample chamber and the optical observation system such that the object is in best focus at a predetermined point of the focus range as the object moves.

12. The apparatus of claim 9, wherein the radial motion control, the focus motion control and the azimuthal motion control are combined to generate a 3-D volumetric scan of motion of the object.

13. The apparatus of claim 9, further comprising translational motion control of a relative position of the sample chamber and the optical observation system;
   wherein the translational motion control and the azimuthal motion control both act to compensate for azimuthal motion of the object;
   wherein a frequency range for the azimuthal motion control is from 0-10 Hz;
   wherein a frequency range for the translational motion control is from 10-100 Hz.

14. The apparatus of claim 9, further comprising a thermal enclosure within which the sample chamber and the optical observation system are enclosed.

15. The apparatus of claim 9, wherein the optical observation system is a horizontally mounted microscope, and wherein all control of relative position of the optical observation system and the sample chamber is generated by motion of the sample chamber.

16. The apparatus of claim 9, wherein the radial motion control and the focus motion control include closed-loop control.

17. The apparatus of claim 1,
   wherein a terrestrial gravitational field is present at a location of the apparatus; and
   wherein the apparatus is configured such that the azimuthal motion of the object is substantially up or down with respect to the terrestrial gravitational field.

* * * * *